(12) United States Patent
Wakita

(10) Patent No.: US 8,148,565 B2
(45) Date of Patent: Apr. 3, 2012

(54) METHOD OF MANUFACTURING AN ORGANIC SILICON COMPOUND THAT CONTAINS A METHACRYLOXY GROUP OR AN ACRYLOXY GROUP

(75) Inventor: Keiji Wakita, Midland, MI (US)

(73) Assignee: Dow Corning Toray Company, Ltd., Chiyoda-ku, Tokyo (JP)

( * ) Notice: Subject to any disclaimer, the term of this patent is extended or adjusted under 35 U.S.C. 154(b) by 551 days.

(21) Appl. No.: 12/064,208

(22) PCT Filed: Aug. 9, 2006

(86) PCT No.: PCT/JP2006/316075
§ 371 (c)(1),
(2), (4) Date: Jul. 30, 2009

(87) PCT Pub. No.: WO2007/020932
PCT Pub. Date: Feb. 22, 2007

(65) Prior Publication Data
US 2009/0306370 A1    Dec. 10, 2009

(30) Foreign Application Priority Data
Aug. 19, 2005  (JP) ................. 2005-238465

(51) Int. Cl.
*C07D 279/18* (2006.01)
(52) U.S. Cl. ....................... 556/436; 556/440
(58) Field of Classification Search .............. 556/436, 556/440
See application file for complete search history.

(56) References Cited

U.S. PATENT DOCUMENTS

| | | | |
|---|---|---|---|
| 4,338,474 A | 7/1982 | Jackisch | |
| 4,465,881 A | 8/1984 | Miller et al. | |
| 5,378,775 A | 1/1995 | Shimizu et al. | |
| 6,001,937 A | 12/1999 | Krishnamurti et al. | |

FOREIGN PATENT DOCUMENTS

| | | |
|---|---|---|
| EP | 0247501 A2 | 12/1987 |
| EP | 0334500 A1 | 9/1989 |
| EP | 0496397 A1 | 7/1992 |
| EP | 520477 A1 | 12/1992 |
| EP | 562584 A1 | 9/1993 |
| EP | 0693492 A1 | 1/1996 |
| EP | 1234830 A2 | 8/2002 |
| GB | 1196676 | 7/1970 |
| JP | 62283983 A | 12/1987 |
| JP | WO 8900993 A1 | 2/1989 |
| JP | 1165581 A | 6/1989 |
| JP | 05186478 A | 7/1993 |
| JP | 05230143 A | 9/1993 |
| JP | 07025907 A | 1/1995 |
| JP | 2001-023687 | 1/2001 |
| JP | 2003-252851 A | 9/2003 |

OTHER PUBLICATIONS

English language abstract for JP1165581 extracted from espacenet.com database, dated Oct. 28, 2008.
English language abstract for JP62283983 extracted from espacenet.com database, dated Oct. 27, 2008.
English language translation and abstract for JP05186478 extracted from PAJ database, dated Oct. 28, 2008, 90 pages.
English language translation and abstract for JP05230143 extracted from PAJ database, dated Oct. 28, 2008, 49 pages.
English language translation and abstract for JP07025907 extracted from PAJ database, dated Oct. 28, 2008, 30 pages.
English language translation and abstract for JP2001-023687 extracted from PAJ database, dated Oct. 28, 2008, 65 pages.
English language translation and abstract for JP2003-252851 extracted from PAJ database, dated Oct. 28, 2008, 36 pages.
PCT International Search Report for PCT/JP2006/316075, dated Jan. 18, 2007, 5 pages.

*Primary Examiner* — Kahsay T Habte
(74) *Attorney, Agent, or Firm* — Howard & Howard Attorneys PLLC

(57) ABSTRACT

A method of manufacturing an organic silicon compound that contains a methacryloxy group or an acryloxy group is characterized by the fact that manufacturing or conducting purification by distillation is carried out in the presence of a phenothiazine derivative having a molecular weight equal to or higher than 240. A stable composition comprises the organic silicon compound that contains a methacryloxy group or an acryloxy group and the phenothiazine derivative having a molecular weight equal to or higher than 240. The phenothiazine derivative is used in an amount sufficient to stabilize the organic silicon compound.

6 Claims, No Drawings

METHOD OF MANUFACTURING AN ORGANIC SILICON COMPOUND THAT CONTAINS A METHACRYLOXY GROUP OR AN ACRYLOXY GROUP

RELATED APPLICATIONS

This application claims priority to and all the advantages of International Patent Application No. PCT/JP2006/316075, filed on Aug. 9, 2006, which claims priority to Japanese Patent Application No. 2005-238465, filed on Aug. 19, 2005.

TECHNICAL FIELD

The present invention relates to a novel method of manufacturing an organic silicon compound that contains a methacryloxy group or an acryloxy group and that is widely used as a silane coupling agent and a polymerizable monomer.

BACKGROUND ART

Since under the effect of heat that is generated either during industrial-scale synthesis or during purification by distillation, organic silicon compounds that contain methacryloxy groups or acryloxy groups are subject to spontaneous polymerization, and selection of polymerization inhibitors for preventing the undesired spontaneous polymerization is a matter of great importance.

Japanese Unexamined Patent Application Publication [hereinafter referred to as Kokai] S62-283983 (equivalent to EP 0247501) discloses a manufacturing method where an aromatic sulfur compound represented by phenothiazine is used as an inhibitor during distillation and synthesis of an organic silane that contains methacryloxy and acryloxy groups. However, during purification by distillation, the phenothiazine is easily mixed with fractions, and since the final product is admixed with phenothiazine, it is subject to severe coloration.

Kokai H5-186478 (equivalent to EP 0520477) discloses inhibition of polymerization of an acryloxysilane and methacryloxy silane by adding to the composition an N,N-dialkylaminomethylene phenol. Kokai H5-230143 discloses a polymerization inhibitor having an active ingredient in the form of an isocyanuric acid hydroxybenzyl ester derivative, e.g., isocyanuric acid tris(3,5-di-tert-butyl-4-hydroxybenzyl)ester. Kokai H7-25907 discloses a polymerization inhibitor having an active ingredient in the form of a 2,6-di-t-butyl-4-hydroxymethylphenol. Although the last-mentioned polymerization inhibitors are relatively resistant to coloration when mixed with the final product, they are still unsuitable for production under conditions of high temperature and strong acidity inherent in an industrial manufacturing process.

DISCLOSURE OF INVENTION

It is an object of the present invention to provide an efficient method for manufacturing a high-quality, coloration-resistant organic silicon compound that contains a methacryloxy group or an acryloxy group and inhibits spontaneous polymerization under conditions of high temperature and strong acidity inherent in an industrial manufacturing process.

The inventors herein have found that a high-quality organic silicon compound that contains a methacryloxy group or an acryloxy group can be produced without risk of coloration and without spontaneous polymerization, even under vigorous production conditions, if the manufacturing process is carried out with the use of a phenothiazine derivative having a molecular weight no less than 240. Thus the inventors arrived at the present invention.

More specifically, the method of the invention for manufacturing an organic silicon compound that contains a methacryloxy group or an acryloxy group consists of manufacturing or conducting purification by distillation the product either in the presence of a phenothiazine derivative having a molecular weight above at least 240.

The aforementioned phenothiazine derivative is a compound selected from the group consisting of the following: a phenothiazine substituted with alkyl having four or more carbon atoms, dibenzophenothiazine, phenothiazine substituted with acyl having 2 to 18 carbon atoms, N,N' phenothiazine dimer, a compound represented by formula (1) given below:

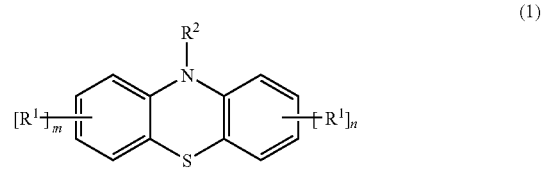

(where $R^1$ is an aralkyl group having 7 to 18 carbon atoms, and $R^2$ is selected from a hydrogen atom or an alkyl group having 1 to 18 carbon atoms, an aralkyl group having 7 to 18 carbon atoms, and an acyl group having 2 to 18 carbon atoms; "m" and "n" are integers from 0 to 2, and where the following condition is satisfied: $m+n \geq 1$), and a compound of the following formula (2):

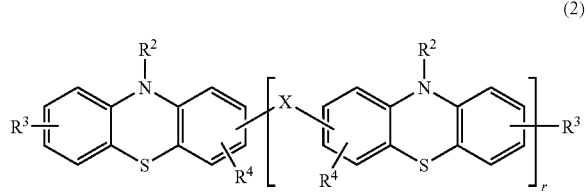

(where $R^2$ is the same as defined above, $R^3$ is either a hydrogen atom or is selected from the group consisting of an alkyl group having 1 to 18 carbon atoms, an aralkyl group having 7 to 18 carbon atoms, and an acyl group having 2 to 18 carbon atoms; $R^4$ is either a hydrogen atom or is selected from an alkyl group having 1 to 18 carbon atoms or an acyl group having 2 to 18 carbon atoms; X is a group selected from a methylene group, α-methylmethylene group, and α-phenylmethylene group; and "r" is a number represented by an average value between 1 and 5. Preferable phenothiazine derivatives of the aforementioned type are compounds selected from the group consisting of 3-(α-methylbenzyl)phenothiazine, 1-(α-methylbenzyl)phenothiazine, 3.7-bis(α-methylbenzyl)phenothiazine, 3-(α,α-dimethylbenzyl)phenothiazine, 3,7-(α,α-dimethylbenzyl)phenothiazine, 10-acetylphenothiazine, and 3,3'-methylene-bis(phenothiazine).

The aforementioned organic silicon compound that contains a methacryloxy group or an acryloxy group can be represented by the following formula (3):

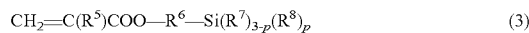

(where $R^5$ is a hydrogen atom or a methyl group, $R^6$ is a bivalent organic group, $R^7$ is an alkyl group, and $R^8$ is either a halogen atom or is selected from an alkoxy group or an alkyloxyalkoxy group; and "p" is an integer from 1 to 3). Most preferable is the organic silicon compound of the aforementioned type, wherein $R^8$ in formula (3) is a bromine atom or a chlorine atom.

Furthermore, a stable composition that contains the aforementioned methacryloxy- or acryloxy-containing organic silicon compound can be prepared by combining the aforementioned organic silicon compound with a phenothiazine derivative that has a molecular weight of 240 or greater and that is used in an amount sufficient for stabilizing the compound, and by subjecting the organic silicon compound to purification by distillation prior to use.

Since the method of the invention inhibits spontaneous polymerization under severe production conditions of high temperature and strong acidity inherent in an industrial manufacturing process and since purification by distillation completely removes the polymerization inhibitor which constitutes a source of coloration of the target product, it becomes possible to efficiently produce a high-quality, coloration-resistant organic silicon compound that contains a methacryloxy group or an acryloxy group.

BEST MODE FOR CARRYING OUT THE INVENTION

Phenothiazine derivatives suitable for the purposes of the present invention may be comprised of known phenothiazine derivatives having molecular weights equal to or greater than 240, preferably greater than 300, and even more preferably, greater than 400.

Such phenothiazine derivatives may be exemplified by the following compounds: 3-t-butyl-phenothiazine, 3-t-amylphenothiazine, 10-t-butyl-phenothiazine, 3-(1,1,3,3-tetramethylbutyl)phenothiazine, or similar phenothiazines substituted with alkyls having four or more carbon atoms; 1,2-benzophenothiazine, or similar benzophenothiazines; 1,2,6,7-benzophenothiazine, or similar benzophenothiazine; 1-acetylphenothiazine, 10-acetylphenothiazine, or similar diphenothiazines substituted with acyls having 2 to 18 carbon atoms; 10,10'-diphenothiazine, 1,1'-dimethyl-10,10'-diphenothiazine, 2,2',6,6'-tetramethyl-10,10'-diphenothiazine, or similar N,N'-phenothiazine dimmers; a compound of following formula (1):

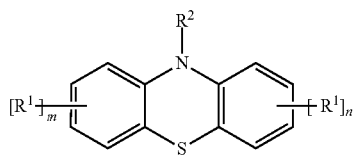

and a compound of following formula (2):

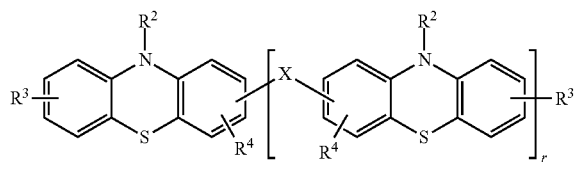

Most preferable from the viewpoint of availability is the compound of formula (1).

In the above formulae, $R^1$ designates benzyl groups, α-methylbenzyl groups, α,α-dimethylbenzyl groups, or similar aralkyl groups having 7 to 18 carbon atoms or 7 to 12 carbon atoms, α-methylbenzyl groups and α,α-dimethylbenzyl groups being preferable; groups designated by $R^1$ may be the same or different.

$R^2$ designates hydrogen atoms or groups selected from linear-chain or branch-chain alkyl groups having 1 to 18 carbon atoms, preferably 1 to 5 carbon atoms, acetyl groups and aralkyl groups having 7 to 18 carbon atoms, preferably, 7 to 12 carbon atoms, and benzoyl groups or similar acyl groups having 2 to 18 carbon atoms, preferably, 2 to 7 carbon atoms. Most preferable are hydrogen atoms or acetyl groups, especially, hydrogen atoms.

$R^3$ designates hydrogen atoms or groups selected from linear-chain or branch-chain alkyl groups having 1 to 18 carbon atoms, preferably 1 to 5 carbon atoms, acetyl groups and aralkyl groups having 7 to 18 carbon atoms, preferably, 7 to 12 carbon atoms, and benzoyl groups or similar acyl groups having 2 to 18 carbon atoms, preferably, 2 to 7 carbon atoms. Preferable are hydrogen atoms, aralkyl groups having 7 to 12 carbon atoms, but most preferable are hydrogen atoms, benzyl groups, α-methylbenzyl groups, α,α-dimethylbenzyl groups, and especially, hydrogen atoms.

$R^4$ designates hydrogen atoms or groups selected from linear-chain or branch-chain alkyl groups and acetyl groups having 1 to 18 carbon atoms, preferably 1 to 5 carbon atoms, and benzoyl groups or similar acyl groups having 2 to 18 carbon atoms, preferably, 2 to 7 carbon atoms. Preferable are hydrogen atoms or acetyl groups.

X designates a group selected from a methylene group, α-methylmethylene group, and α-phenylmethylene group; "m" and "n" are integers from 0 to 2 that satisfy the following condition: "(m+n)≧1"; "r" is a number represented by an average value of 1 to 5 and that preferably is in the range of 1 to 2, and even more preferably, in the range of 1 to 1.5.

The following are specific examples of preferable compound of formula (1): 3-(α-methylbenzyl)phenothiazine, 1-(α-methylbenzyl)phenothiazine, 3,7-bis(α-methylbenzyl)phenothiazine, 3-(α,α-dimethylbenzyl)phenothiazine, and 3,7-bis(α,α-dimethylbenzyl)phenothiazine.

Compounds of formula (2) may be exemplified by compounds of the formulae given below, where "r" is the same as defined above:

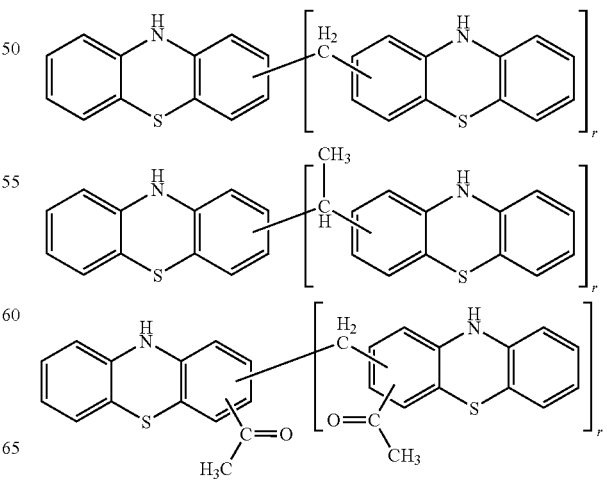

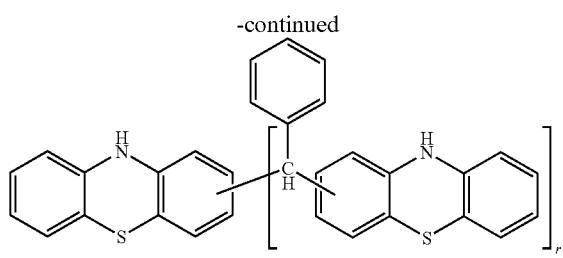

The aforementioned phenothiazine derivatives, even in small quantities, produce a sufficient effect on organic silicon compounds that contain methacryloxy or acryloxy groups. The best results are obtained when, in terms of a weight ratio, the phenothiazine derivative is mixed with the aforementioned organosilicon compound in an amount of 10 to 5000 ppm, preferably 100 to 2000 ppm.

The aforementioned phenothiazine derivatives are suitable for use in the manufacture of an organic silicon compound of below-given formula (3) that contains a methacryloxy group or an acryloxy group:

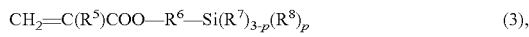

where $R^5$ is a hydrogen atom or a methyl group, and $R^6$ is a bivalent organic group, preferable of which are methylene, ethylene, propylene, butylenes, isobutylene, or similar alkylene groups; $R^7$ is an alkyl group, preferably, methyl group; and $R^8$ is either a chlorine atom, bromine atom or a similar halogen atom or is selected from a methoxy group, ethoxy group, or a similar alkoxy group, or a methoxyethoxy group, ethoxymethoxy group, or a similar alkyloxyalkoxy group. Most preferable are methoxy groups, ethoxy groups, chlorine atoms, or bromine atoms, especially, chlorine atoms or bromine atoms. In the above formula, "p" is an integer from 1 to 3. The following are specific examples of the aforementioned organic silicon compounds: methacryloxymethyl trimethoxysilane, methacryloxypropyl trimethoxysilane, acryloxypropyl trimethoxysilane, methacryloxypropyl methyldimethoxysilane, methacryloxypropyl triethoxysilane, acryloxypropyl triethoxysilane, methacryloxypropyl trichlorosilane, methacryloxypropyl methyldichlorosilane, methacryloxypropyl dimethylchlorosilane, methacryloxyisobutyl trimethoxysilane, and methacryloxyisobutyl trichlorosilane.

Methacryloxy- and acryloxy-containing organic silicon compounds, other than those mentioned above, may be exemplified by bis(methacryloxypropyl) tetramethyldisiloxane, methacryloxypropyl tris(trimethylsiloxy)siloxane, acryloxytrimethylsilane, methacryloxytrimethylsilane, methacryloxyphenyldimethylsilane, or the like.

The aforementioned phenothiazine derivatives can also efficiently inhibit spontaneous polymerization in organic silicon compounds of formula (3) that have methacryloxy or acryloxy groups where $R^8$ in the above formula is a halogen atom. Since such a methacryloxy- or acryloxy-containing organic silicon compounds are strongly acidic and therefore are more readily subject to spontaneous polymerization, they have to be handled with caution.

The aforementioned phenothiazine derivatives can be easily and completely removed from a crude methacryloxy- or acryloxy-containing organic silicon compounds by distillation. The distillation operation can be carried out without the use of a distillation column, with the use of a distillation column, by distillation in vacuum, by thin-film distillation, or by any other known method of distillation. Any of the above distillation methods protects the methacryloxy- or acryloxy-containing organic silicon compounds from mixing with phenothiazine derivatives, and thus prevents coloration of the target product. Furthermore, since the entire phenothiazine derivative remains in the reactor, polymerization is efficiently prevented also in the reactor that may create a problem during distillation.

The aforementioned phenothiazine derivative alone demonstrates sufficient polymerization inhibiting capacity, but, if necessary, it can be additionally combined with known polymerization inhibitors, such as hindered-phenol or amine-type polymerization inhibitors. In the case of distillation, in particular, in order to inhibit polymerization of a gaseous phase, it is recommended to combine the phenothiazine derivative of the invention with p-methoxyphenol, 2,6-di-t-butyl-4-methylphenol, or similar polymerization inhibitors that have boiling points under atmospheric pressure below 300° C.

EXAMPLES

The invention will be further described more specifically with reference to the Practical Examples which are given below. It is understood that these examples should not construed as limiting the scope of the invention.

Practical Example 1

A methacryloxypropyl trichlorosilane was synthesized by a known method where allyl methacrylate and trichlorosilane were used as starting materials. 20 g of the obtained product and 5 mg of a styrenated phenothiazine (ANTAGE STDP-N, molecular weight was 407.6; the product of Kawaguchi Chemical Company, Ltd.) was sealed in a bottle with a threaded cap and heated in a 150° C. oil bath. The obtained product was not gelled and maintained flowability even 20 hours after the above-described treatment.

Formula (4)

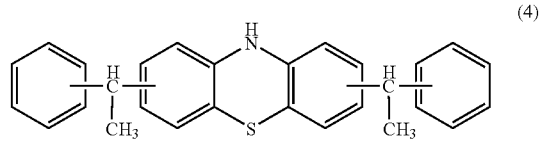

Practical Example 2

The product was obtained by the same method as in Practical Example 1, except that 5 mg of a 10-acetylphenothiazine of below-given formula (5) were used instead of the styrenated phenothiazine of formula (4). The obtained product was not gelled and maintained flowability even 20 hours after the above-described treatment.

[Formula 5]

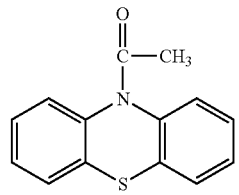

The 10-acetylphenothiazine of formula (5) was synthesized by the following method. A 200-ml four-neck flask was loaded with 19.93 g (0.1 mole) of phenothiazine, 15.31 g (0.15 mole) of acetic anhydride, and 40 g of xylene, and the contents were subjected to heating under reflux conditions for 6 hours. The reaction liquid was cooled, the precipitate was separated by filtering, and the product washed with methanol. As a result, 22.6 g of 10-acetylphenothiazine having a molecular weight of 241.3 were obtained.

Practical Example 3

The product was obtained by the same method as in Practical Example 1, except that 2.5 mg of a phenothiazine derivative of below-given formula (6) were used instead of the styrenated phenothiazine of formula (4). The obtained product was not gelled and maintained flowability even 20 hours after the above-described treatment.

[Formula 6]

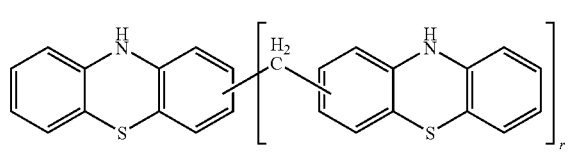

(6)

The phenothiazine derivative of formula (6) was synthesized by the following method. A 200-ml four-neck flask was loaded with 4.98 g (0.25 mole) of phenothiazine and 18 g of tetrahydrofuran, and then a mixture composed of 6.0 g of a concentrated hydrochloric acid, 4.36 g of formalin, and 24 g of methanol was added dropwise at room temperature. The precipitate was separated by filtering, and the product was washed with methanol. As a result, 3.11 g of phenothiazine oligomer were obtained.

NMR analysis and gel-permeation chromatography (GPC) confirmed that the product had the structure of formula (6) where "r" was on average about 1.2 and molecular weight was on average about 453.

Comparative Examples 1 to 10

The products were obtained by the same method as in Practical Example 1, except that known polymerization inhibitors of the type shown in Table 1 were used instead of the styrenated phenothiazine. Within 10 hours after the preparation, the products were gelled and lost flowability.

Practical Example 4

A four-neck flask equipped with a stirrer was loaded with 867 g (6.87 mole) of allyl methacrylate, 0.2 g of a platinum-divinyltetramethylsiloxane complex (0.4 mmole of metallic platinum), and 2.7 g of a styrenated phenothiazine (ANTAGE STDP-N, molecular weight was 407.6; the product of Kawaguchi Chemical Company, Ltd.). The content was heated at 80° C., and 912 g (6.73 mole) of trichlorosilane were added dropwise. Following this, 647 g (20.2 mole) of methanol were added dropwise, and the product was neutralized by blowing ammonia into the product. The precipitate was separated by filtering, the product was distilled under a reduced pressure of 7 mmHg, and a 115 to 122° C. fraction was taken. The obtained fraction comprised 1229 g of a methacryloxypropyl trimethoxysilane which was obtained with the yield of 74%. For two days the obtained product was exposed to direct sun rays, but no changes in color were observed.

Practical Example 5

The product was obtained by the same method as in Practical Example 4, except that 1.6 g (6.6 mmole) of a 10-acetylphenothiazine of formula (5) were used instead of the styrenated phenothiazine of formula (4). The obtained fraction comprised 1203 g of a methacryloxypropyl trimethoxysilane which was obtained with the yield of 72%. For two days the obtained product was exposed to direct sun rays, but no changes in color were observed.

Practical Example 6

The product was obtained by the same method as in Practical Example 4, except that 1.4 g of a phenothiazine derivative of formula (6) were used instead of the styrenated phenothiazine of formula (4). The obtained fraction comprised 1171 g of a methacryloxypropyl trimethoxysilane which was obtained with the yield of 70%. For two days the obtained product was exposed to direct sun rays, but no changes in color were observed.

Comparative Example 11

The product was obtained by the same method as in Practical Example 4, except that phenothiazine was used instead of the styrenated phenothiazine of formula (4). For two days the obtained product was exposed to direct sun rays, and the color was changed to brown.

Comparative Example 12

The product was obtained by the same method as in Practical Example 4, except that 2,6-di-t-butyl-4-methylphenol was used instead of the styrenated phenothiazine of formula (4). A polymer was formed in the reactor in the final stage of distillation, and further distillation could not be continued.

TABLE 1

| Examples | Polymerization Inhibitors | Time to Gelling |
|---|---|---|
| Appl. Ex. 1 | Styrenated phenothiazine | No gelling after 20 hr. |
| Appl. Ex. 2 | 10-Acetylphenathiazene | No gelling after 20 hr. |
| Appl. Ex. 3 | 3,3'-Methylene bis (phenothiazine) | No gelling after 20 hr. |
| Comp. Ex. 1 | p-methoxyphenol | Gelling within 1 hr. |
| Comp. Ex. 2 | Hydroquinone | Gelling within 1 hr. |
| Comp. Ex. 3 | t-butylpyrocatecol | Gelling within 1 hr. |
| Comp. Ex. 4 | 2,6-di-t-butyl-4-methylphenol | Gelling after 3 hr. |
| Comp. Ex. 5 | 2,6-di-t-butyl-4-dimethyl-aminomethylphenol | Gelling after 8 hr. |
| Comp. Ex. 6 | 4,4'-thio-bis (6-t-butyl-3-methylphenol) | Gelling within 1 hr. |
| Comp. Ex. 7 | N-nitroso-phenylhydroxylamine hydrochloride salt | Gelling within 1 hr. |
| Comp. Ex. 8 | 2,4-bis (n-octylthio)-6-(4-hydroxy-3,5-di-t-butylanilino)-1,3,5-triazine | Gelling after 4 hr. |
| Comp. Ex. 9 | Pentaerythritol tetrakis [3-(3,5-di-t-butyl-4-hydroxyphenyl) propionate | Gelling within 1 hr. |
| Comp. Ex. 10 | 1,3,5-trimethyl-2,4,6-tris (3,5-di-t-butyl-4-hydroxybenzyl) benzene | Gelling within 1 hr. |

The invention claimed is:
1. A method of manufacturing an organic silicon compound that contains a methacryloxy group or an acryloxy group, wherein said organic silicon compound that contains a methacryloxy group or an acryloxy group is a compound represented by the following formula (3):

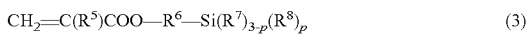

(where $R^5$ is a hydrogen atom or a methyl group, $R^6$ is a bivalent organic group, $R^7$ is an alkyl group, and $R^8$ is either a halogen atom or is selected from an alkoxy group or an alkyloxyalkoxy group; and "p" is an integer from 1 to 3), the method being characterized by the fact that manufacturing or conducting purification by distillation is carried out in the presence of a phenothiazine derivative having a molecular weight equal to or higher than 240, wherein said phenothiazine derivative is a compound selected from the following: an alkyl-substituted phenothiazine with said alkyl group having four or more carbon atoms, dibenzophenothiazine, an acyl-substituted phenothiazine with said acyl group having 2 to 18 carbon atoms, an N,N' phenothiazine dimer, a compound represented by formula (1) given below:

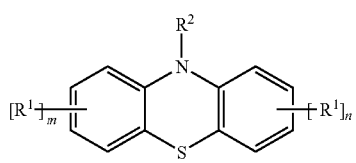

(where $R^1$ is an aralkyl group having 7 to 18 carbon atoms, and $R^2$ is selected from a hydrogen atom or an alkyl group having 1 to 18 carbon atoms, an aralkyl group having 7 to 18 carbon atoms, and an acyl group having 2 to 18 carbon atoms; "m" and "n" are integers from 0 to 2, and where the following condition is satisfied: m+n≧1), and a compound of the following formula (2):

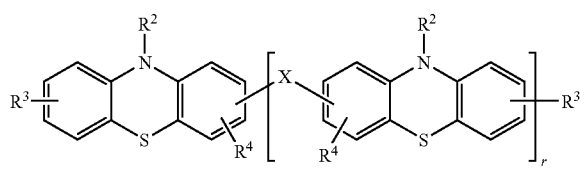

(where $R^2$ is the same as defined above, $R^3$ is either a hydrogen atom or is selected from an alkyl group having 1 to 18 carbon atoms, an aralkyl group having 7 to 18 carbon atoms, and an acyl group having 2 to 18 carbon atoms; $R^4$ is either a hydrogen atom or is selected from an alkyl group having 1 to 18 carbon atoms or an acyl group having 2 to 18 carbon atoms; X is a group selected from a methylene group, α-methylmethylene group, and α-phenylmethylene group; and "r" is a number represented by an average value between 1 and 5.

2. The method of claim 1 for manufacturing an organic silicon compound that contains a methacryloxy group or an acryloxy group, wherein said phenothiazine derivative is selected from the following compounds: 3-(α-methylbenzyl)phenothiazine, 1-(α-methylbenzyl)phenothiazine, 3.7-bis(α-methylbenzyl)phenothiazine, 3-(α,α-dimethylbenzyl)phenothiazine, 3,7-(α,α-dimethylbenzyl)phenothiazine, 10-acetylphenothiazine, and 3,3'-methylene-bis(phenothiazine).

3. The method of claim 1 for manufacturing an organic silicon compound that contains a methacryloxy group or an acryloxy group, wherein $R^8$ in formula (3) is a bromine atom or a chlorine atom.

4. A stable composition comprising an organic silicon compound that contains a methacryloxy group or an acryloxy group, wherein said organic silicon compound that contains a methacryloxy group or an acryloxy group is a compound represented by the following formula (3):

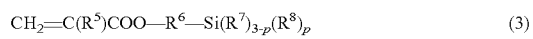

(where $R^5$ is a hydrogen atom or a methyl group, $R^6$ is a bivalent organic group, $R^7$ is an alkyl group, and $R^8$ is either a hydrogen atom or is selected from an alkoxy group or an alkyloxyalkoxy group; and "p" is an integer from 1 to 3), and a phenothiazine derivative having a molecular weight equal to or higher than 240 and used in an amount sufficient to stabilize the aforementioned organic silicon compound, wherein said phenothiazine derivative is a compound selected from the following:

an alkyl-substituted phenothiazine with said alkyl group having four or more carbon atoms, dibenzophenothiazine, an acyl-substituted phenothiazine with said acyl group having 2 to 18 carbon atoms, an N,N' phenothiazine dimer, a compound represented by formula (1) given below:

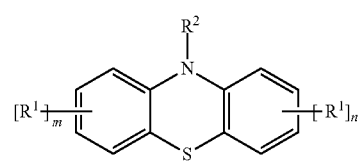

(where $R^1$ is an aralkyl group having 7 to 18 carbon atoms, and $R^2$ is selected from a hydrogen atom or an alkyl group having 1 to 18 carbon atoms, an aralkyl group having 7 to 18 carbon atoms, and an acyl group having 2 to 18 carbon atoms; "m" and "n" are integers from 0 to 2, and where the following condition is satisfied: m+n≧1), and a compound of the following formula (2):

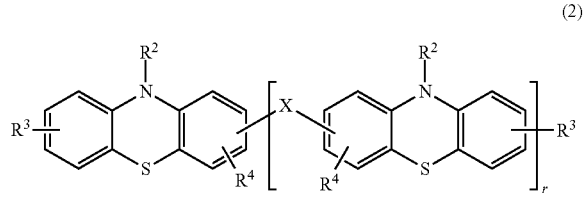

(where $R^2$ is the same as defined above, $R^3$ is either a hydrogen atom or is selected from an alkyl group having 1 to 18 carbon atoms, an aralkyl group having 7 to 18 carbon atoms, and an acyl group having 2 to 18 carbon atoms; $R^4$ is either a hydrogen atom or is selected from an alkyl group having 1 to 18 carbon atoms or an acyl group having 2 to 18 carbon atoms; X is a group selected from a methylene group, α-methylmethylene group, and α-phenylmethylene group; and "r" is a number represented by an average value between 1 and 5.

5. A method of manufacturing an organic silicon compound that contains a methacryloxy group or an acryloxy group, characterized by removing a phenothiazine derivative as a result of distillation purification of the composition according to claim 4.

6. The stable composition of claim 4, wherein said phenothiazine derivative is selected from the following compounds: 3-(α-methylbenzyl)phenothiazine, 1-(α-methylbenzyl)phenothiazine, 3.7-bis(α-methylbenzyl)phenothiazine, 3-(α,α-dimethylbenzyl)phenothiazine, 3,7-(α,α-dimethylbenzyl)phenothiazine, 10-acetylphenothiazine, and 3,3'-methylene-bis(phenothiazine).

* * * * *